United States Patent [19]

Lundh et al.

[11] Patent Number: 4,790,841

[45] Date of Patent: Dec. 13, 1988

[54] DEVICE FOR BAG-SHAPED LIQUID-CONTAINERS FOR SICK-CARE

[75] Inventors: Karl-Erik Lundh, Gislaved; Tore Kers, Upsala, both of Sweden

[73] Assignee: Gislaved Plastindustri AB, Sweden

[21] Appl. No.: 445,372

[22] PCT Filed: Mar. 31, 1982

[86] PCT No.: PCT/SE82/00102

§ 371 Date: Nov. 24, 1982

§ 102(e) Date: Nov. 24, 1982

[87] PCT Pub. No.: WO82/03332

PCT Pub. Date: Oct. 14, 1982

[30] Foreign Application Priority Data

Mar. 31, 1981 [SE] Sweden ............................... 8102059

[51] Int. Cl.$^4$ ............................................. A61B 19/00

[52] U.S. Cl. .................................... 604/408; 604/415

[58] Field of Search ............... 604/408, 415, 403, 905, 604/283; 150/8; 215/247, 255, 296, 305, 320

[56] References Cited

U.S. PATENT DOCUMENTS

| | | | |
|---|---|---|---|
| 2,689,562 | 9/1954 | Adams et al. | 604/415 |
| 3,606,077 | 9/1971 | Faust | 604/415 |
| 3,915,212 | 10/1975 | Bujan et al. | 604/408 |
| 4,187,893 | 2/1980 | Bujan | 604/415 |
| 4,298,045 | 11/1981 | Weiler et al. | 604/415 |
| 4,303,067 | 12/1981 | Connolly et al. | 604/408 |
| 4,439,192 | 3/1984 | Leurink | 604/415 |

*Primary Examiner*—John D. Yasko

*Attorney, Agent, or Firm*—Ostrolenk, Faber, Gerb & Soffen

[57] ABSTRACT

A sealing device for bag-shaped, liquid containers for sick-care of flexible material. An opening for filling or emptying the container is sealed by means of a disc-shaped member which has a tube made in one piece therewith and extending in use towards the interior of the container. One end of the tube adjacent the disc-shaped member being closed by a cover which seals against the outside surface of the disc-shaped member level therewith, and the other end of the tube is sealed by means of a flattening of the tube, to produce a sterile space between the two closed ends of the tube, said flattened portion of the tube extending transversely to the longitudinal direction of the tube to form two tube sidewall portions converging towards the flattened portion of the tube, at least one of said sidewall portions being penetrable by a cannula when inserted through the mouth of the tube and extending through the tube.

2 Claims, 1 Drawing Sheet

DEVICE FOR BAG-SHAPED LIQUID-CONTAINERS FOR SICK-CARE

Figure 2:
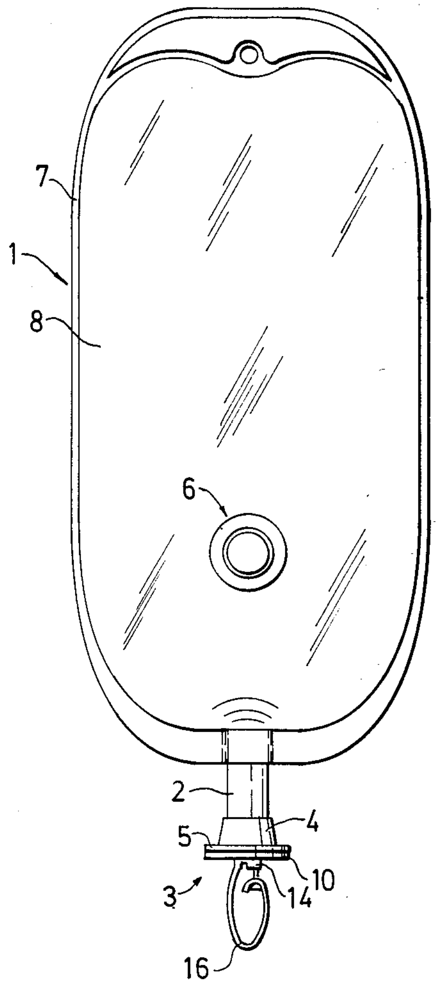

The present invention relates to a device for bag-shaped liquid containers for sick care of flexible material consisting of one or more flat plastic films fused at the edges or a folded-over fused plastic film, and comprising at least one opening for filling or emptying the container.

This type of liquid container is used for a number of different purposes in sick-care, e.g. for administering intravenously nutrients and blood substitute. These areas of use involve the storage and tapping of liquid. These liquid containers are provided with filling and tapping openings, which have the shape of a flanged funnel. This type of opening facilitates filling the container with liquid, which is usually done under sterile conditions at the supplier of the liquid in question. After filling the container, it is sealed by means of a suitable type of plug, which for use permits access by means of a cannula to the contents of the container. In order to prevent contamination of the cannula as it is inserted into the medium in the container, up to now a sealing device has been used which is provided under a cover with a sealing, sterile membrane. After removing the cover, the cannula can be inserted into the liquid in the container by puncturing the membrane thereby avoiding contact with non-sterilized surfaces. With this type of sealing device, it has proved difficult to find the cannula insertion hole with the cannula behind the membrane directly after puncture. Furthermore, the cover covering the opening provided with a membrane to the container is difficult to remove. Manufacturing considerations make it necessary that the sterilization of this type of sealing device be carried out in several stages, since it is made of three different parts which are fused together into one part, which involves relatively high manufacturing costs.

The purpose of the present invention is to remove the disadvantages which are to be found in previously used sealing devices of this type and to achieve a device which is essentially characterized by a disc formation sealing the opening and having a tube made in one piece therewith and extending towards the interior of the container, one end of said tube terminating in an integrally made cover which seals against the outside of the disc formation level therewith, the other end of said tube terminating in a closing portion by means of a flattening of the tube, for achieving a sterile space between the two closed ends of the tube.

By virtue of the invention a device is now achieved which eminently achieves its purposes but is at the same time simple and inexpensive to manufacture. One reason for this is that the sealing device according to the invention is made in one piece and sterilization need only be done once during manufacture, since the material at the flattened end of the tube permits the passage of steam. The design of the cover permits easy and reliable removal of the same for use, i.a. because the straight pulling of the pull loop provides a concentration of force to a point in the material in the region between the lower edge portion of the cover and the disc formation. After removing the cover, a cannula can be easily inserted into the liquid in the container by virtue of the fact that prior to the puncturing of the portion of the tube near the inner flattened portion, which has a thinner material thickness, the cannula is guided through the sterile space by the sidewalls of the tube. After puncture, the cannula is effectively retained in its inserted position in the sealing device according to the invention by the friction created between the cannula and the tube by firstly the projections at the mouth of the tube and secondly at the hole produced by the cannular when penetrating through the tube wall next to the flattened portion.

Figure 1:
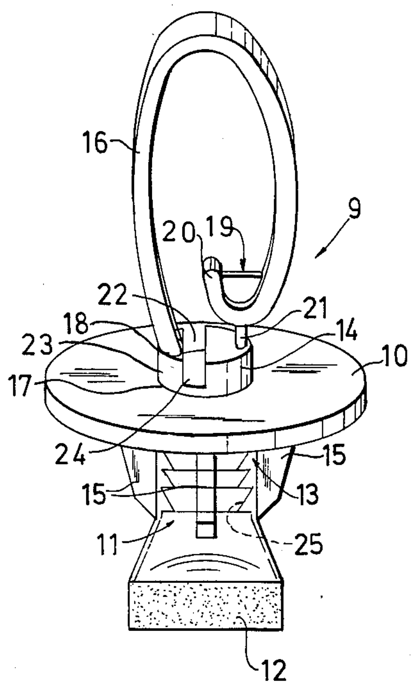

The invention will be described in more detail below with reference to the accompanying drawing, in which an embodiment selected as an example of the sealing device is shown in FIG. 1 in perspective and in FIG. 2 as a side-view of the sealing device mounted in the opening of a liquid container.

The liquid container 1 shown as an example is provided with a pipe 2 as a filling and emptying opening 3. The pipe 2 is made with a funnel-shaped portion 4 which has a flange 5 around its opening. The liquid container 1 can also be provided with a device 6 for opening the interior of the container 1, e.g. for inserting extra nutrients to the liquid in the container 1. The liquid container 1 consists of two flat, plastic films 8 fused at the edges 7, which form the sides or walls of the container 1. The filling and tapping opening 3 of the container 1 is sealed after filling the container 1 with the liquid in question by means of a sealing device 9, consisting of a disc formation 10 covering the funnel-shaped portion 4 and in sealing contact with the flange 5. The fixing of the disc formation 10 against the flange can also be done by means of heat or a suitable adhesive. A tube 11 is made in one piece with the disc formation 10 and extends towards the interior of the container 1 into the pipe 2 when assembled. The inner end of the tube 11 terminates in a flattened portion 12 sealed against the interior of the tube 11, and its other outer end or mouth 13 terminates in a cover 14 made in one piece with and sealing against the outside of the disc formation 10. The tube 11 has a thinner material thickness immediately before the flattened portion 12 to make possible not only penetration of a cannula but passage of steam in sterilization as well.

The sealing device 9 according to the invention is made of a plastic material, e.g. injection-molded polyvinyl chloride. The flattening of the portion 12 is suitably done at the same time as or immediately after the injection-molding of the sealing device 9, producing a sterile space between the cover 14 and the flattened portion 12. For orientation when mounting the sealing device 9 on the flanged opening 3, guide flanges 15 are disposed on the tube 11 next to the disc formation 10. To retain a cannula, the tube 11 has at its inlet a plurality of projections 25. The cover 14, which is made in one piece with the disc formation 10 and the tube 11, can be torn off by means of a grip loop 16 from the disc formation 10 to expose the mouth 13 of the tube. The cover 14 closes the mouth 13 along a tear initiation line 17 of thin material thickness at the transition between the cover 14, the tube 11 and the disc formation 10. The grip loop 16 extends integrally from the top, peripheral edge portion 18 of the cover 14 and ends in a grip portion 19, which can be made with one or two grip tabs 20. The grip portion 19 can be easily detachably fixed to the cover 14 by means of a thin string of material 21. To achieve a concentration of force to a point to tear off the cover 14 along the tear initiation line 17, a cavity 22 is arranged diagonally across the top of the cover 14 in the vicinity of the anchoring location of the grip loop 16 in the edge portion 18 of the cover 14. For removal of the cover 14, the grip portion 19 is first detached from the cover 14 by breaking the material string 21. When the grip loop 16 is then pulled away from the disc formation 10, a concentration of force to a point is obtained which begins the actual tearing along the tear initiation line 17, by bending the portion 23 of the cover 14 from which the grip loop 16 stems towards the logitudinal direction of the cavity 22 with the bottom portion 24 of the cavity 22 serving as sort of fold line. A cannula (not shown) can then be inserted into the tube 11, puncture the same immediately before the flattened portion 12 and thereafter 12 and therefore come into contact with the liquid in the container 1.

What is claimed is:

1. Sealing device for bag-shaped liquid containers of flexible material for sick care comprising one of more flat plastic films fused together along their edges, or a folded-over plastic film fused together at its free edges, and having at least one opening for filling and emptying the container, the sealing device comprising a disc-shaped member for sealing the opening and having a tube made in one piece therewith and extending in use towards the interior of the container, the end of the tube adjacent the disc-shaped member being closed by a cover which seals against the outside surface of the disc-shaped member level therewith and can be torn off around the mouth of the tube, the other end of the tube being sealed by means of a flattening of the tube, said flattened portion of the tube extending transversely to the longitudinal direction of the tube to form two tube sidewall portions converging towards the flattened portion of the tube, at least one of said sidewall portions being penetrable by a cannula when inserted through the mouth of the tube and extending through the tube, wherein the wall thickness of the tube at and immediately before the flattened portion is thinner than that of the rest of the tube such as to permit steam to pass in sterilization.

2. Sealing device for bag-shaped liquid containers of flexible material for sick care comprising one of more flat plastic films fused together along their edges, or a folded-over plastic film fused together at its free edges, and having at least one opening for filling and emptying the container, the sealing device comprising a disc-shaped member for sealing the opening and having a tube made in one piece therewith and extending in use towards the interior of the container, the end of the tube adjacent the disc-shaped member being closed by a cover which seals against the outside surface of the disc-shaped member level therewith and can be torn off around the mouth of the tube, the other end of the tube being sealed by means of a flattening of the tube, said flattened portion of the tube extending transversely to the longitudinal direction of the tube to form two tube sidewall portions converging towards the flattened portion of the tube, at least one of said sidewall portions being penetrable by a cannula when inserted through the mouth of the tube and extending through the tube, wherein the tube where joined to the dis-shaped member has on its outside at least three radially extending guide flanges for fixing the position of the disc-shaped member during assembly in the case where the opening of the liquid container is made as a funnel-shaped portion interacting with the disc-shaped member and the tube.

* * * * *